United States Patent [19]

Furuya

[11] Patent Number: 4,788,443
[45] Date of Patent: Nov. 29, 1988

[54] APPARATUS FOR MEASURING PARTICLES IN A FLUID

[75] Inventor: Yoshiyuki Furuya, Hino, Japan

[73] Assignee: Kowa Company Ltd., Aichi, Japan

[21] Appl. No.: 59,734

[22] Filed: Jun. 8, 1987

[30] Foreign Application Priority Data

Jun. 6, 1986 [JP] Japan ................... 61-130061

[51] Int. Cl.⁴ .................... G01N 15/02; G01D 5/36
[52] U.S. Cl. ................... 250/574; 250/222.2;
356/336; 356/338; 73/865.5
[58] Field of Search ............ 250/574, 222.2, 374;
356/335–343; 73/865.5, 36

[56] References Cited

U.S. PATENT DOCUMENTS 4,035,080 7/1977 Yamaguchi .................. 250/574
4,521,521 6/1985 Abbott et al. ................. 250/574
4,676,641 6/1987 Bott ............................. 356/336

Primary Examiner—Edward P. Westin
Assistant Examiner—Charles F. Wieland
Attorney, Agent, or Firm—Bruce L. Adams; Van C. Wilks

[57] ABSTRACT

An apparatus for measuring particles in a fluid comprises a laser source for producing a laser beam which is projected onto the fluid containing the particles. Laser light scattered by the particles is converted into an electrical signal consisting of pulses corresponding to the particles to be measured. The pulses are counted by first and second counters and processed in a processor to derive therefrom the diameter and/or concentration of the particles. The first and second counters are alternately operated for pulse counting and inhibited from pulse counting. Each counter transfers its count to the processor during the period that it is inhibited from counting.

3 Claims, 5 Drawing Sheets

APPARATUS FOR MEASURING PARTICLES IN A FLUID

BACKGROUND OF THE INVENTION

1. Field of the Invention

This invention relates to an apparatus for measuring particles in a fluid, more particularly to an apparatus for measuring the diameter and concentration of particles in a fluid by the photon counting method.

2. Description of the Prior Art

In conventional apparatuses of this type, the fluid containing particles to be measured is placed in a measurement cell and irradiated with a laser beam, and the characteristics of the particles are determined from the light scattered by the particles using a photomultiplier.

The light scattered by a particle in the fluid becomes weaker in proportion as the diameter of the particle becomes smaller, and it is known that in carrying out detection with respect to weak light, it is more effective to use the photomultiplier in accordance with a photon counting method than to use it in an analogue manner.

The conventional apparatus will first be explained with reference to FIGS. 4 and 5.

In FIG. 4, a laser beam from a laser beam source 1 is condensed on a measurement region 3 by a lens 2. The measurement region 3 is within a measurement cell 4 through which a fluid flows. When particles pass through the measurement regions, they scatter the incident laser light. Light scattered by the particle is focused by a lens 5 to form an image at a slit 6, and the light passing through the slit 6 advances to the photocathode of a photomultiplier tube 7 which serves as a photoelectric converter. This light can be considered to be constituted of particles, i.e. photons, and the photons reaching the photocathode cause electrons to be emitted from the same photocathode by the photoelectric effect. The electrons emitted from the photocathode are multiplied in number within the photomultiplier tube 7 by a factor of approximately $10^6$ and output as a signal from the photomultiplier tube. This output signal is amplified by a preamplifier 8 and then passed through a peak discriminator 9 which serves as a pulse generator. The threshold value of the peak discriminator 9 is set at the lower limit of the voltage or current value corresponding to the signal at the time when a single electron is emitted from the photocathode of the photomultiplier 7. When the signal amplified by the preamplifier 8 is greater than the threshold value of the peak discriminator 9, the peak discriminator 9 outputs a pulse. This pulse is sent to a pulse shaper 10 where it is shaped.

The shaped pulses output by the pulse shaper 10 are called "photoelectron pulses" and the method involving the counting of these photoelectron pulses is the "photon counting method." In the photon counting method, the number of photoelectron pulses per unit time is proportional to the intensity of the scattered light from the particle. Therefore, by counting the number of photoelectron pulses per fixed time interval, it becomes possible to measure the intensity of the scattered light from particle.

In FIG. 4, the photoelectron pulses output from the pulse shaper 10 are counted in a pulse counter 11. The pulse counter 11 is initialized by a reset signal output from a processor system. The count value of the pulse counter 11 is latched by a latch circuit 12 from which it is read by a processor 13. The latch circuit 12 is controlled by a read signal from the processor 13.

As shown in greater detail in FIG. 5A, this conventional apparatus consists of a single pulse counter 11, a latch circuit 12 for latching the count value of the pulse counter 11, and a processor 13 for reading the count latched in the latch circuit and for controlling the pulse counter and latch circuit.

As shown in FIG. 5B, this arrangement results in photoelectron pulses 15 being applied to a terminal 14 of the pulse counter 11 independently of and without relation to the read and reset signals output by the processor 13. When a predetermined period of time has lapsed after the start of pulse counting by the pulse counter 11, a read signal 16 is issued to cause the count value of the pulse counter 11 to be latched by the latch circuit 12. After the count value of the pulse counter 11 has been latched by the latch circuit 12, the pulse counter 11 is initialized by a reset signal 17. At this time, the pulse width T of the reset signal has to be made longer than the time constant determined by a resistor R and a capacitor C which are provided to prevent malfunction of the pulse counter 11 because of noise.

When the reset signal 17 becomes low level, the pulse counter 11 resumes the counting state and the counting of the photoelectron pulses resumes. The count value latched by the latch circuit 12 is read during the period that the read signal from the processor 13 is at high level. By repeating these operations, it is possible to count the number of photoelectron pulses within fixed time intervals.

When the photoelectron pulses are counted by the aforesaid conventional method, the processor 13 cannot read the photoelectron pulses 15 input to the pulse counter 11 during the time L indicated in FIG. 5B. This means that there is a blind period during which the photoelectron pulses are not counted, so that there arises an error in the measurement of the concentration of the particles in the fluid.

SUMMARY OF THE INVENTION

An object of the invention is to provide an apparatus for measuring particles in a fluid which has no blind period and is able to count the photoelectron pulses with high accuracy.

According to the present invention there is provided an apparatus for measuring particles in a fluid by irradiating the fluid containing the particles with a laser beam and analyzing the laser light scattered by the particle to determine the diameter and/or concentration of the particles, the apparatus comprising a laser beam source for producing a laser beam, an optical system for irradiating the fluid containing the particles with the laser light and focusing laser light scattered by the particle, a photoelectric converter for receiving laser light scattered by said particle and converting the same into an electrical signal, a pulse generator for generating pulses in response to said electrical signal, the number of pulses corresponding to the diameter of particles, first and second pulse counters for counting the pulses from the pulse generator, and a processor for processing the pulse count from the first and second pulse counters to derive therefrom the diameter and/or concentration of said particles, the first and second pulse counters being alternately operated for pulse counting.

According to a preferred embodiment of the invention the first and second counters are operated alternately such that one counts pulses while the other is inhibited from counting pulses, the count of each counter being read into the processor while it is inhibited from counting pulses.

Thus the arrangement has two pulse counters for counting the pulses and when one of the pulse counters is counting photoelectron pulses, the other is in a non-counting state during which the processing system reads its count value. As a result, it is possible to carry out uninterrupted counting of the photoelectron pulses independently of the pulse counting operation, whereby no blind period arises and the photoelectron pulses can be counted accurately.

BRIEF DESCRIPTION OF THE DRAWINGS

The objects and features of the present invention will become more apparent from a consideration of the following detailed description taken in conjunction with the accompanying drawings in which.

DETAILED DESCRIPTION OF THE PREFERRED EMBODIMENTS

An embodiment of the invention will now be described in detail with reference to FIGS. 1 to 3.

Figure 1:
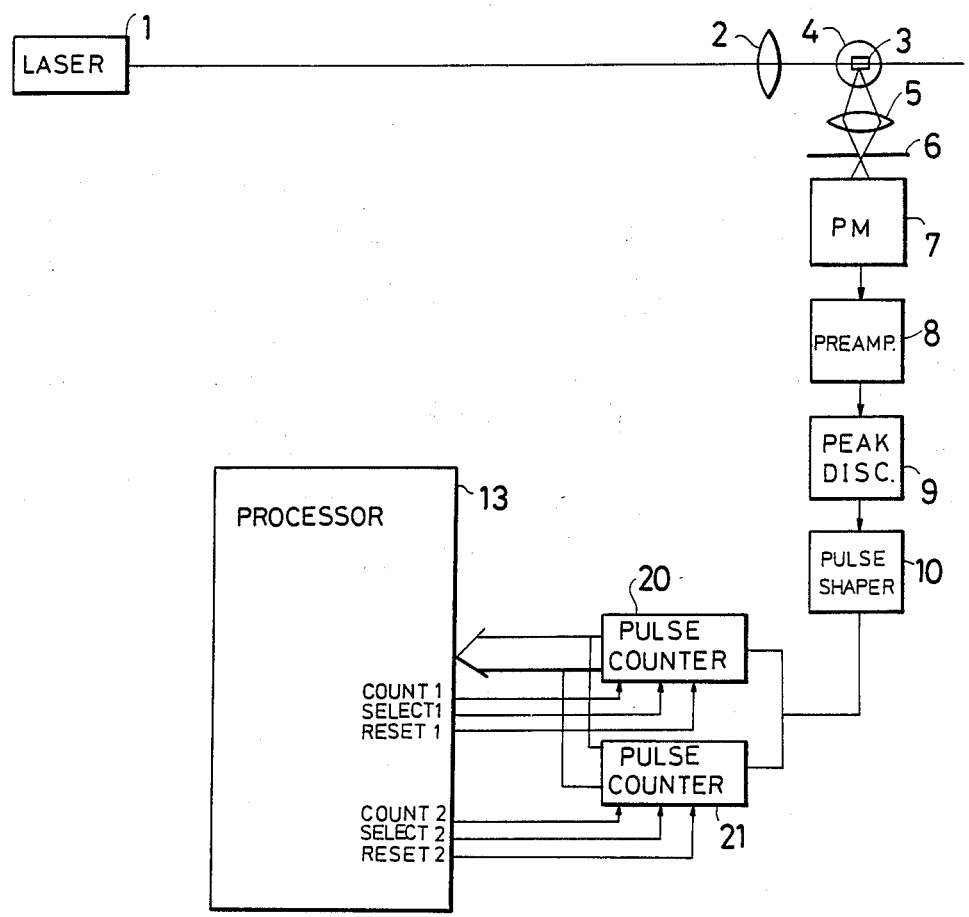
FIG. 1 is a block diagram schematically illustrating the structure of the apparatus according to the present invention.

The structure of the apparatus according to the invention is shown in FIG. 1. Components thereof that are identical with those in FIG. 4 are denoted by like reference numerals and will not be explained again here.

Figure 4:
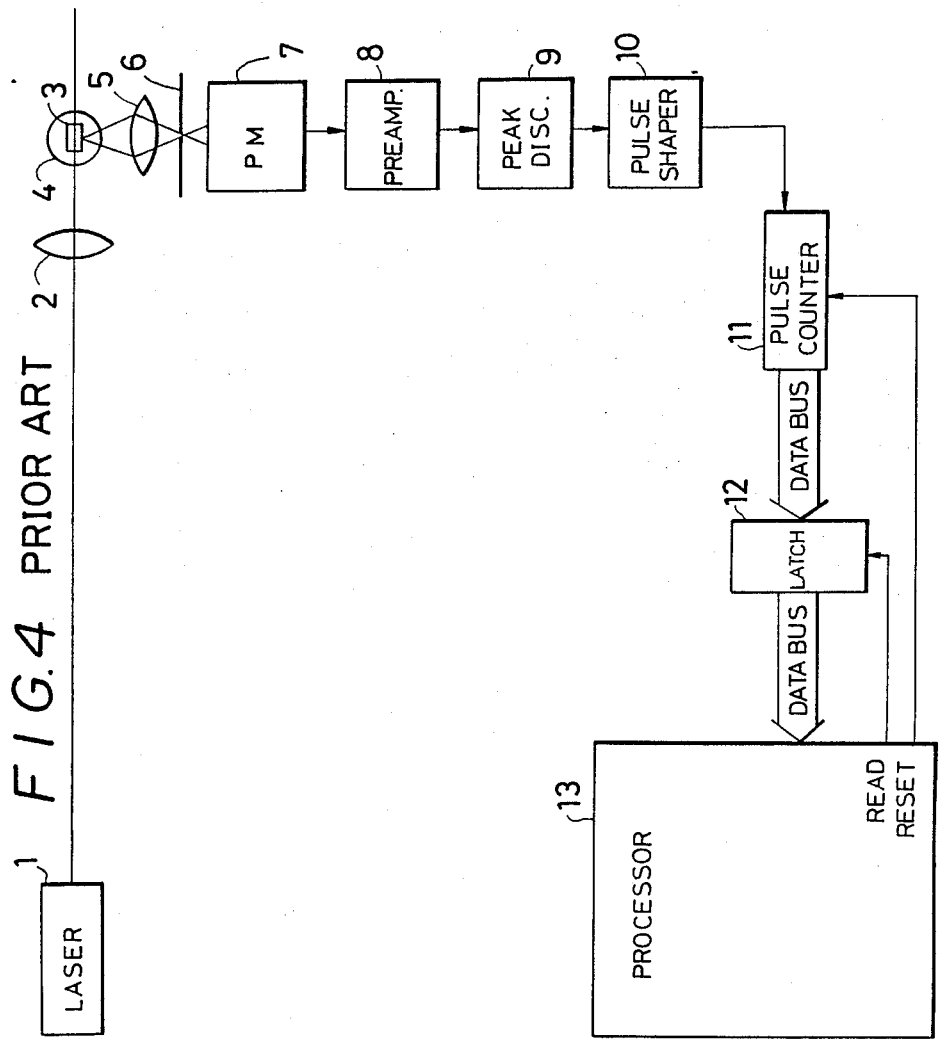
FIG. 4 is a block diagram of a prior art apparatus.
Figure 5A:
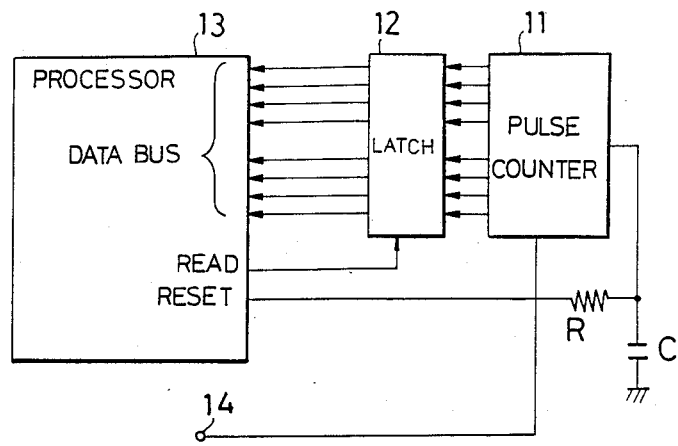
FIGS. 5A and 5B are a detailed block diagram and a signal waveform diagram for explaining the structure and operation of the prior art apparatus of FIG. 4.
Figure 5B:
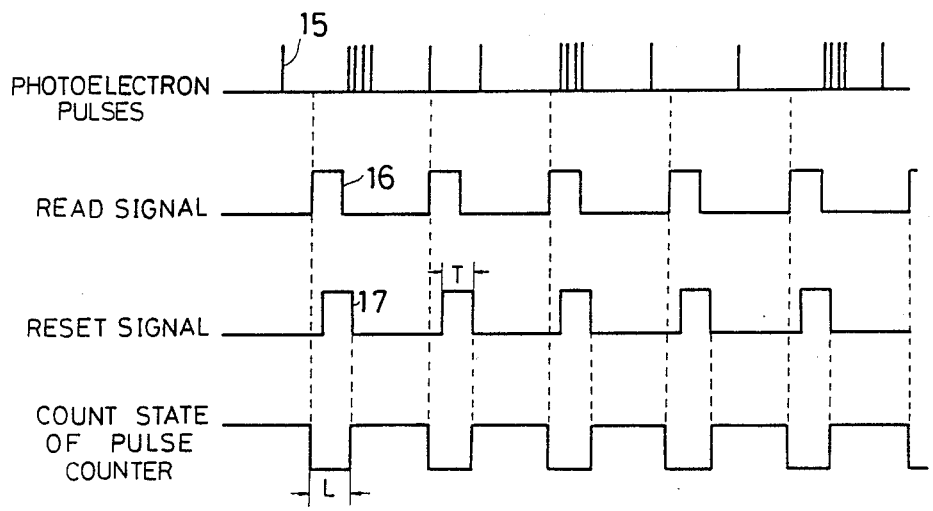

The apparatus according to the invention is the same as that illustrated in FIG. 4 up to and including the step in which the photoelectron pulses are obtained. It differs in that it has two pulse counters 20, 21.

Figure 2:
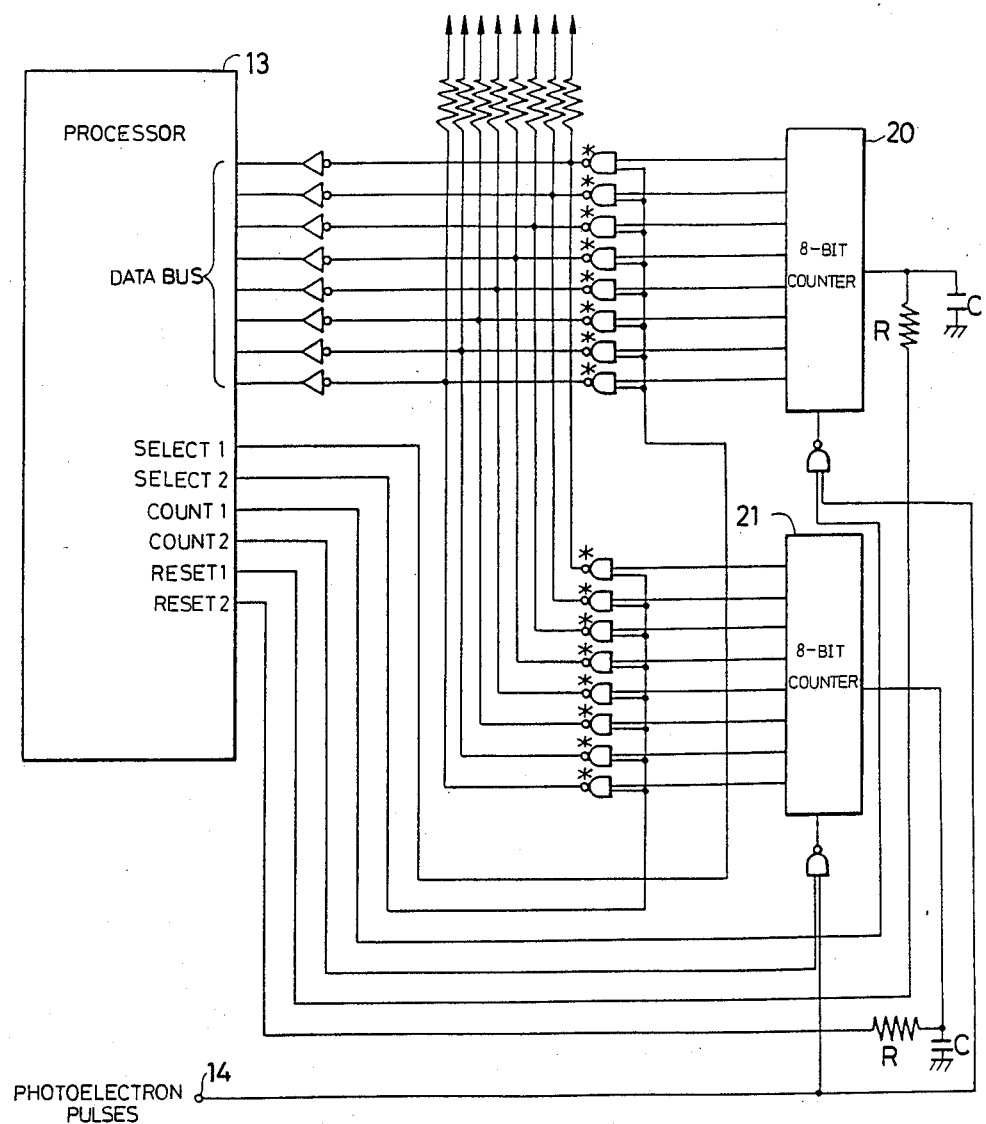
FIG. 2 is a detailed block diagram of the same.
Figure 3:
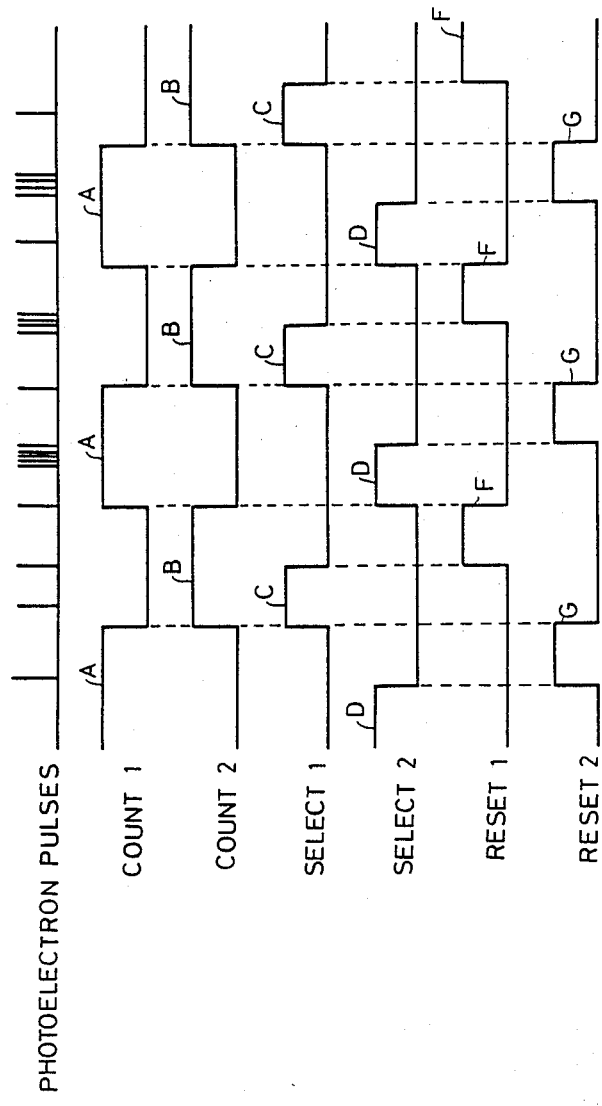
FIG. 3 is a signal waveform diagram for explaining the operation of the apparatus illustrated in FIGS. 1 and 2.

As shown in detail in FIG. 2, the pulse counters 20, 21 are constituted as 8-bit counters which alternate once every fixed time period in counting the photoelectron pulses input through the terminal 14. The selection between the pulse counter 20 and the pulse counter 21 is carried out by count 1 and count 2 control signals sent by the processor 13 to the pulse counters 20 and 21. Here it should be understood that the pulse counters 20 and 21 are never simultaneously in the counting state. The selection as to which count value is to be read by the processor 13, that of the pulse counter 20 or that of the pulse counter 21, is carried out by select 1 and select 2 control signals sent by the processor 13 to the pulse counters 20 and 21. The processor 13 reads the count value from the selected pulse counter via a data bus.

The operation of the aforesaid apparatus will now be explained with reference to FIG. 3.

First, when the processor 13 in FIGS. 1 and 2 causes the count 1 control signal to assume high level, the 8-bit counter 20 is selected for counting the photoelectron pulses, and when it causes the count 2 control signal to assume high level, the 8-bit counter 21 is selected for counting the photoelectron pulses. The count 1 and count 2 control signals never become high level at the same time.

For reading the count value of the 8-bit counter 20, the processor 13 first stops the photoelectron pulse counting operation of the 8-bit counter 20 by switching the count 1 control signal to low level and then prepares the 8-bit counter 20 for reading of its count value by switching the select 1 control signal to high level, whereafter it reads the count value. Similarly, for reading the count value of the 8-bit counter 21, the processor 13 first stops the photoelectron pulse counting operation of the 8-bit counter 21 by switching the count 2 control signal to low level and then prepares the 8-bit counter 21 for reading of its count value by switching the select 2 control signal to high level, whereafter it reads the count value. The select 1 and 2 control signals are never made high level simultaneously.

Further, the processor 13 initializes the 8-bit counter 20 by switching the reset 1 control signal to high level, and initializes the 8-bit counter 21 by switching the reset 2 control signal to high level. The high-level pulse widths of reset 1 and reset 2 are made longer than the time constant determined by a resistor R and a capacitor C. The resistor R and capacitor C are provided to prevent noise-induced malfunction of the 8-bit counters 20 and 21.

In this state, if photoelectron pulses are input to the terminal 14, the 8-bit counter 20 will count these photoelectron pulses during the period that the count 1 control signal is at its high level A. During this same period, the 8-bit counter 21 does not count photoelectron pulses. After the lapse of a predetermined fixed period, the count 1 control signal is switched to low level and, simultaneously, the count 2 control signal is switched to its high level B. By this operation the 8-bit counter 20 stops counting photoelectron pulses and the 8-bit counter 21 starts counting them.

For reading the count value of the 8-bit counter 20 which has now stopped counting photoelectron pulses, the processor 13 switches the select 1 control signal to its high level C. Following this, while the select 1 control signal remains at high level, the processor 13 reads the count value of the 8-bit counter 20. After completing a read-out of the count value of the 8-bit counter 20, the processor 13 switches the select 1 control signal to low level and switches the reset 1 control signal to its high level F, whereby the 8-bit counter 20 is initialized.

Upon the lapse of a predetermined fixed period after the 8-bit counter 21 starts counting photoelectron pulses, the processor 13 switches the count 1 control signal to its high level and, simultaneously, the reset 1 control signal and the count 2 control signal are switched to their low levels. By this operation, the 8-bit counter 20 starts counting photoelectron pulses and the 8-bit counter 21 stops counting them.

For reading the count value of the 8-bit counter 21 which has now stopped counting photoelectron pulses, the processor 13 switches the select 2 control signal to its high level D. Following this, while the select 1 control signal remains at high level, the processor 13 reads the count value of the 8-bit counter 21. After completing a read-out of the count-value of the 8-bit counter 21, the processor 13 switches the select 2 control signal to low level and switches the reset 2 control signal to its high level G, whereby the 8-bit counter 21 is initialized.

The foregoing operation is thereafter repeatedly carried out, whereby the counting of the photoelectron pulses by the photon counting method is repeatedly carried out for fixed time intervals.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An apparatus for measuring particles in a fluid by irradiating the fluid containing the particles with a laser beam and analyzing the laser light scattered by the particles to determine at least one of the diameter and concentration of the particles, the apparatus comprising:

a laser beam source for producing a laser beam;

an optical system for irradiating the fluid containing the particles with the laser beam and focusing laser light scattered by the particles;

a photoelectric converter for receiving laser light scattered by said particles and focused by the optical system and converting the same into an electrical signal, a pulse generator for generating pulses in response to said electrical signal, the number of pulses corresponding to the diameter and concentration of said particles, first and second pulse counters for counting the pulses from the pulse generator; and a processor for processing the pulse count from the first and second pulse counters to derive therefrom at least one of the diameter and concentration of said particles, including means for alternately operating said first and second pulse counters for pulse counting comprising means for generating a first count signal to activate the first pulse counter and deactivate the second pulse counter, means for generating a second count signal to activate the second pulse counter and deactivate the first pulse counter, means for generating a first select signal in synchronism with the generation of the second count signal to deactivate the first pulse counter and to read the count in the first pulse counter, means for generating a second select signal in synchronism with the generation of the first count signal to deactivate the second pulse counter and to read the count in the second pulse counter, means for generating a first reset signal to reset the count of the first pulse counter after the reading of its contents and before the generating of the next first count signal to initiate the counting by the first pulse counter, and means for generating a second reset signal to reset the count of the second pulse counter after the reading of its contents and before generating the next second count signal to initiate the counting by the second pulse counter.

2. An apparatus according to claim 1, wherein said first and second counters are operated alternately such that one counts pulses while the other is inhibited from counting pulses, the count of each counter being read into the processor while it is inhibited from counting pulses.

3. In an apparatus for measuring particles in a fluid of the type having a laser beam source for producing a laser beam to irradiate the fluid, means for converting light scattered by the particles into pulses corresponding in number to particle diameter and concentration and means for counting the number of pulses per a predetermined time period, the improvement wherein the means for counting the number of pulses per predetermined time period comprises:

a first pulse counter receptive of the pulses and having a data output, a count enable input, a reset input for resetting same and a read input for reading the count at the data output thereof;

a second pulse counting receptive of the pulses and having a data output, a count enable input, a reset input for resetting same and a read input for reading the count at the data output thereof; and processing means for effecting the continuous counting of pulses by the first and second counters comprising means for producing first count enable pulses having an enabling portion having a duration of said predetermined time period and nonenabling portion of the same duration and for applying same to the count enable input of the first counter, means for producing second count enable pulses having an enabling portion having a duration of said predetermined time period during the nonenabling portion of the first count enable pulses and a nonenabling portion having a duration of said predetermined time period during the enabling portion of the first count enable pulses and for applying same to the count enable input of the second counter, means for producing first select pulses during the nonenabling portion of the first count enable pulses and for applying same to the read input of the first counter, means for producing second select pulses during the nonenabling portion of the second count enable pulses and for applying same to the read input of the second counter, means for producing first reset pulses during the nonenabling portions of the first count enable pulses and after the first select pulses and for applying same to the reset input of the first counter and means for producing second reset pulses during the nonenabling portions of the second select pulses and for applying same to the reset input of the second counter.

* * * * *